United States Patent [19]
Baker et al.

[11] Patent Number: 5,541,321
[45] Date of Patent: Jul. 30, 1996

[54] PROCESS FOR THE PREPARATION OF A SUBSTITUTED DIAMINOALCOHOL

[75] Inventors: William R. Baker, Libertyville, Ill.; John K. Pratt, Kenosha, Wis.; Daniel W. Norbeck, Crystal Lake; Chen Zhao, Gurnee, both of Ill.

[73] Assignee: Abbott Laboratories, Abbott Park, Ill.

[21] Appl. No.: 413,660

[22] Filed: Mar. 30, 1995

Related U.S. Application Data

[60] Division of Ser. No. 913,572, Jul. 14, 1992, Pat. No. 5,436,339, which is a continuation-in-part of Ser. No. 795,415, Nov. 20, 1991, Pat. No. 5,229,518, which is a continuation-in-part of Ser. No. 665,635, Mar. 6, 1991, abandoned.

[51] Int. Cl.⁶ .................................................. C07D 213/26
[52] U.S. Cl. .................. 546/14; 546/264; 546/284.4; 546/283.4; 546/269.7; 548/203; 548/204; 548/214; 549/321; 560/157; 564/149; 564/150; 564/355; 564/461; 564/487
[58] Field of Search ............................... 546/14.264, 280, 546/283; 548/203, 204, 214; 549/321; 560/157; 564/150, 149, 355, 461, 487

[56] References Cited

U.S. PATENT DOCUMENTS

| | | | |
|---|---|---|---|
| 4,665,055 | 5/1987 | Evans | 514/18 |
| 4,729,985 | 3/1988 | Kleinman et al. | 514/17 |
| 4,898,977 | 2/1990 | Herold et al. | 564/191 |
| 5,354,866 | 10/1994 | Kemp et al. | 546/265 |

FOREIGN PATENT DOCUMENTS

| | | | |
|---|---|---|---|
| 0486948 | 5/1992 | European Pat. Off. | 546/265 |

*Primary Examiner*—Zinna Northington Davis
*Attorney, Agent, or Firm*—Steven R. Crowley

[57] ABSTRACT

A process is disclosed for the preparation of a substituted diaminoalcohol of the formula:

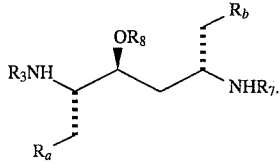

2 Claims, No Drawings

PROCESS FOR THE PREPARATION OF A SUBSTITUTED DIAMINOALCOHOL

This is a division of U.S. patent application Ser. No. 07/913,572, filed Jul. 14, 1992 now U.S. Pat. No. 5,436,339, which is a continuation-in-part of U.S. patent application Ser. No. 795,415, filed Nov. 20, 1991 now U.S. Pat. No. 5,224,518, which is a continuation-in-part of U.S. patent application Ser. No. 665,635, filed Mar. 6, 1991 now abandoned.

TECHNICAL FIELD

The present invention relates to a process for the preparation of a substituted diaminoalcohol.

BACKGROUND OF THE INVENTION

Compounds which are inhibitors of HIV protease are currently being investigated for treatment of HIV infection. Certain HIV protease inhibitors comprise a moiety which is a substituted 2,5-diamino-3-hydroxyhexane. HIV protease inhibitors of particular interest are compounds of the formula 1:

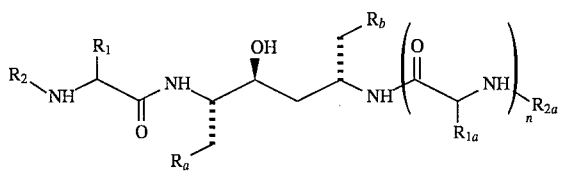

wherein n is 0 or 1, $R_a$ and $R_b$ are independently selected from loweralkyl, cycloalkyl, aryl, alkoxyalkyl, thioalkoxyalkyl and heterocyclic, $R_1$ and $R_{1a}$ are independently selected from loweralkyl and $R_2$ and $R_{2a}$ are independently selected from —C(O)—$R_4$–$R_5$ wherein at each occurrence $R_4$ is independently selected from O, S and —N($R_6$)— wherein $R_6$ is hydrogen or loweralkyl and at each occurrence $R_5$ is independently selected from benzyl, (thiazolyl)methyl and (pyridyl)methyl; or a pharmaceutically acceptable salt, prodrug or ester thereof. Compounds of formula 1 are disclosed in European Patent Application No. EP0486948, published May 27, 1992.

A preferred HIV protease inhibitor is a compound of formula 2:

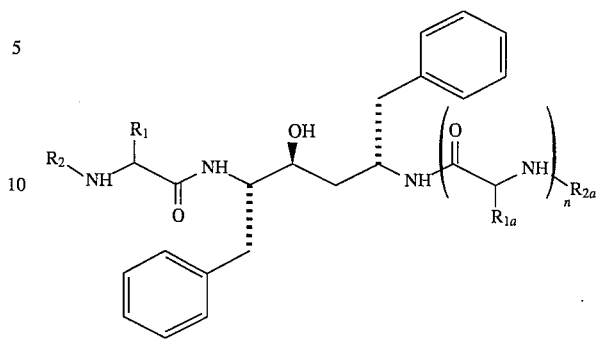

or a pharmaceutically acceptable salt, prodrug or ester thereof,

A more preferred HIV protease inhibitor is a compound of the formula 3.

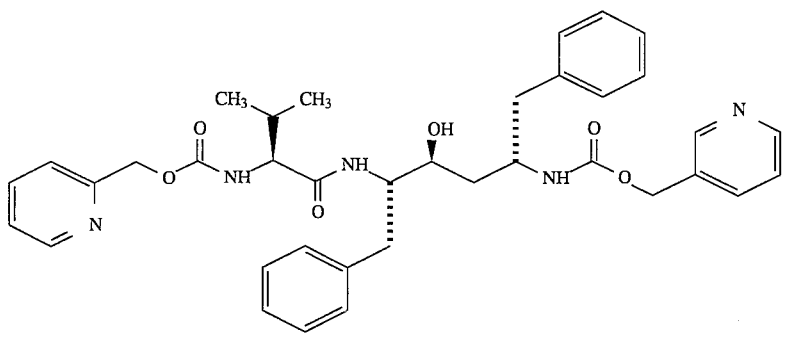

or a pharmaceutically acceptable salt, prodrug or ester thereof.

DISCLOSURE OF THE INVENTION

The present invention relates to a process for the preparation of an intermediate which is useful for the preparation of compounds of formula 1. The intermediate is a compound of formula 4:

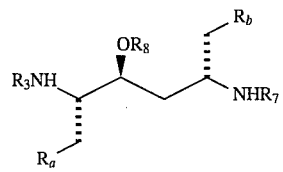

wherein $R_a$ and $R_b$ are independently selected from loweralkyl, cycloalkyl, aryl, alkoxyalkyl, thioalkoxyalkyl and heterocyclic, $R_3$ is hydrogen or an N-protecting group, $R_7$ is hydrogen or —C(O)—O—$R_5$ wherein $R_5$ is selected from benzyl, (thiazolyl)methyl and (pyridyl)methyl and $R_8$ is hydrogen or a hydroxy-protecting group; or a salt thereof. A preferred intermediate is the compound of formula 4 wherein $R_a$ and $R_b$ are phenyl.

A process for the preparation of 4 is shown in Schemes I–IV. In Scheme I, lactone 5 ($R_3$ is an N-protecting group, preferably, t-butyloxycarbonyl or benzyloxycarbonyl and the like) is reacted with a non-nucleophilic strong base (for example, lithium diisopropyl amide (LDA) or lithium hexamethyldisilazide (LiN(TMS)$_2$) or sodium hexamethyldisilazide (NaN(TMS)$_2$) and the like) in an inert solvent (for example, tetrahydrofuran or dimethoxyethane or diethyl ether and the like) at a temperature of from about −80° C. to about −60° C. to form the enolate. The enolate is then alkylated with $XCH_2R_b$, wherein X is a leaving group such as chloro, bromo, iodo, methansulfonate, benzenesulfonate, p-toluenesulfonate, trifluoromethanesulfonate and the like to produce the mixture of diastereomers 6.

Basic hydrolysis of 6 with a strong base (for example, NaOH/dioxane or $LiOH/H_2O/THF$ or KOH/MeOH and the like), followed by reaction with a hydroxy-protecting reagent (for example, t-butyldimethylsilyl chloride or t-butyldiphenylsilyl chloride or trimethylsilyl chloride or dihydropyran or acetic anhydride and the like), provides 7 ($R_8$=hydroxy-protecting group).

Curtius rearrangement of 7 (for example, by reaction with $(PhO)_2PON_3$/triethylamine/toluene; or acid chloride formation by reaction with oxalyl chloride and the like, followed by reaction with an azide such as $NaN_3$ and the like, followed by heating; or other such methods known to one skilled in the art) provides the intermediate isocyanate. Reaction of the isocyanate in situ with $R_5OH$ provides 8 as a mixture of diastereomers which can be separated (for example, by crystallization or chromatography and the like) to give 3 wherein $R_7$ is $—C(O)OR_5$. The hydroxyl-protecting group can be optionally removed by methods known to one skilled in the art, such as reaction with acid (for example, HCl/MeOH or trifluoroacetic acid and the like for acid labile groups) or by reaction with base (for example, LiOH or NaOH and the like for base labile groups) or by fluoride ion (for example, tetrabutylammonium fluoride or cesium fluoride or HF/pyridine and the like) when the protecting group is a silicon derivative. The N-protecting group $R_3$ can optionally be removed using methods known to one skilled in the art (for example, by reaction with acid, such as HCl or trifluororacetic acid and the like for acid labile protecting groups or by hydrogenation for protecting groups such as benzyloxycarbonyl and the like).

Alternatively, $R_5OH$ can be replaced by water to provide 3 wherein $R_7$ is hydrogen. The hydroxyl-protecting group and the N-protecting group can be optionally removed as outilned above.

Scheme II illustrates an alternative preparation of alkylated lactone 6. Lactone ester 8 (R* is loweralkyl or benzyl) is reacted with base (for example, NaOEt/EtOH, NaH/THF or KH/THF and the like) to form the enolate. The enolate is then alkylated with $XCH_2R_b$ wherein X is a leaving group such as chloro, bromo, iodo, methansulfonate, benzenesulfonate, p-toluenesulfonate, trifluoromethanesulfonate and the like to produce 9. Hydrolysis of the ester with strong base, followed by decarboxylation of the resulting carboxylic acid by refluxing in toluene, provides 6.

An alternative preparation of 3 is illustrated in Scheme III. In this alternative method, the separation of diastereomers occurs prior to hydrolysis of the alkylated lactone. This process involves enrichment of the diastereomeric mixture of lactones with the desired diastereomer prior to separation of the diastereomeric mixture. This process is illustrated using the benzylated lactone 10 as a representative example. The process shown in Scheme III can be applied to any alkylated lactone of formula 6.

Lactone 10 is reacted with a non-nucleophilic strong base (for example, lithium diisopropyl amide (LDA) or lithium hexamethyldisilazide ($LiN(TMS)_2$) or sodium hexamethyldisilazide ($NaN(TMS)_2$) and the like) in an inert solvent (for example, tetrahydrofuran or dimethoxyethane or diethyl ether and the like) at a temperature of from about −80° C. to about −60° C. to form the enolate. The enolate is then quenched with from about 3 to about 5 equivalents of a proton source selected from a compound of the formula (i) $CH(R_c)(CO_2Rd)_2$ wherein $R_c$ is hydrogen, loweralkyl, $—SO_2Ph$, $NO_2$ or phenyl and $R_d$ is loweralkyl or benzyl, (ii) Meldrum's acid, (iii) $CH(R_e)(CN)_2$ wherein $R_e$ is hydrogen, loweralkyl or phenyl, (iv) $R_fO_2CCH_2PO(OR_g)_2$ wherein $R_f$ is loweralkyl or benzyl and $R_g$ is loweralkyl and (v) $PhO_2SCH_2CN$ and the like (for example, $CH_2(CO_2Me)_2$, $CH_2(CO_2Et)_2$, $CH_2(CO_2t-Bu)_2$, $CH_2(CO_2CH_2Ph)_2$, Meldrum's acid, $CHMe(CO_2Et)_2$, $CHPh(CO_2Et)_2$, $CHNO_2(CO_2Et)_2$, $CHi-Pr(CO_2Et)_2$, $CH_2(CN)_2$, $EtO_2CCH_2PO(OEt)_2$, $CNCH_2SO_2Ph$ or $Ph-SO_2-CH(CO_2Et)_2$ and the like) at a temperature of from about −80° C. to about −60° C. to provide a mixture of 11a and 11b which is enriched (>2/3)in 11b. The desired isomer 11b can be separated by chromatography or crystallization. A preferred proton source is $CH_2(CO_2Me)_2$, $CH_2(CO_2Et)_2$, $CH_2(CO_2t-Bu)_2$, $CH_2(CO_2CH_2Ph)_2$ or Meldrum's acid.

Basic hydrolysis with strong base (for example, NaOH/dioxane or $LiOH/H_2O/THF$ or KOH/MeOH and the like), followed by reaction with a hydroxy-protecting reagent (for example, t-butyldimethylsilyl chloride or t-butyldiphenylsilyl chloride or trimethylsilyl chloride or dihydropyran or acetic anhydride and the like), provides 12 ($R_8$=hydroxy-protecting group).

Curtius rearrangement of 12 (for example, by reaction with $(PhO)_2PON_3$/triethylamine/toluene; or acid chloride formation by reaction with oxalyl chloride and the like, followed by reaction with an azide such as $NaN_3$ and the like, followed by heating; or other such methods known to one skilled in the art) provides the intermediate isocyanate. Reaction of the isocyanate in situ with $R_5OH$ provides 3 wherein $R_7$ is $—C(O)OR_5$. The hydroxyl-protecting group can be optionally removed by methods known to one skilled in the art, such as reaction with acid (for example, HCl/MeOH or trifluoroacetic acid and the like for acid labile groups) or by reaction with base (for example, LiOH or NaOH and the like for base labile groups) or by fluoride ion (for example, tetrabutylammonium fluoride or cesium fluoride or HF/pyridine and the like) when the protecting group is a silicon derivative. The N-protecting group $R_3$ can optionally be removed using methods known to one skilled in the art (for example, by reaction with acid, such as HCl or trifluororacetic acid and the like for acid labile protecting groups or by hydrogenation for protecting groups such as benzyloxycarbonyl and the like).

Alternatively, $R_5OH$ can be replaced by water to provide 3 wherein $R_7$ is hydrogen. The hydroxyl-protecting group and the N-protecting group can be optionally removed as outlined above.

Scheme IV illustrates a preferred embodiment. Reaction of lactone 13 (J. Org. Chem. 51 3921 (1986)) with LDA, followed by addition of dimethylmalonate, provides a mixture of 14a and 14b in which 14b is the predominant isomer. Isomer 14b is separated from 14a. Isomer 14b is hydrolyzed to the hydroxy acid and the hydroxy group is protected as the t-butyldimethylsilyl ether to give 15. Compound 15 undergoes Curtius rearrangement and reaction with 3-pyridylcarbinol to provide 16. The hydroxy-protecting group $R_8$ and the N-protecting group $R_3$ can optionally be removed.

SCHEME I
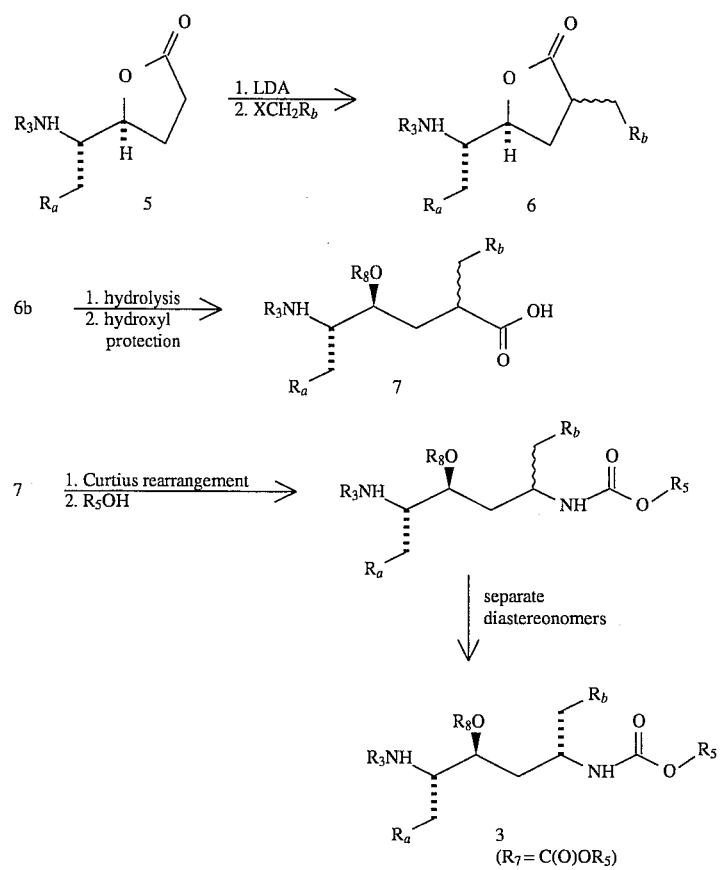
SCHEME II
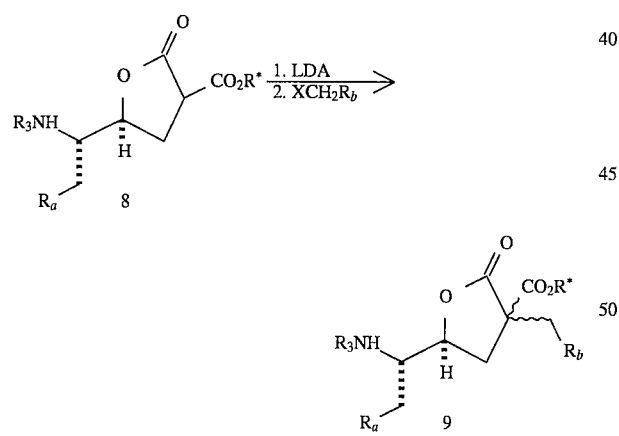
-continued
SCHEME II
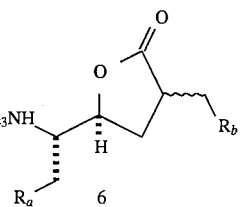

SCHEME III
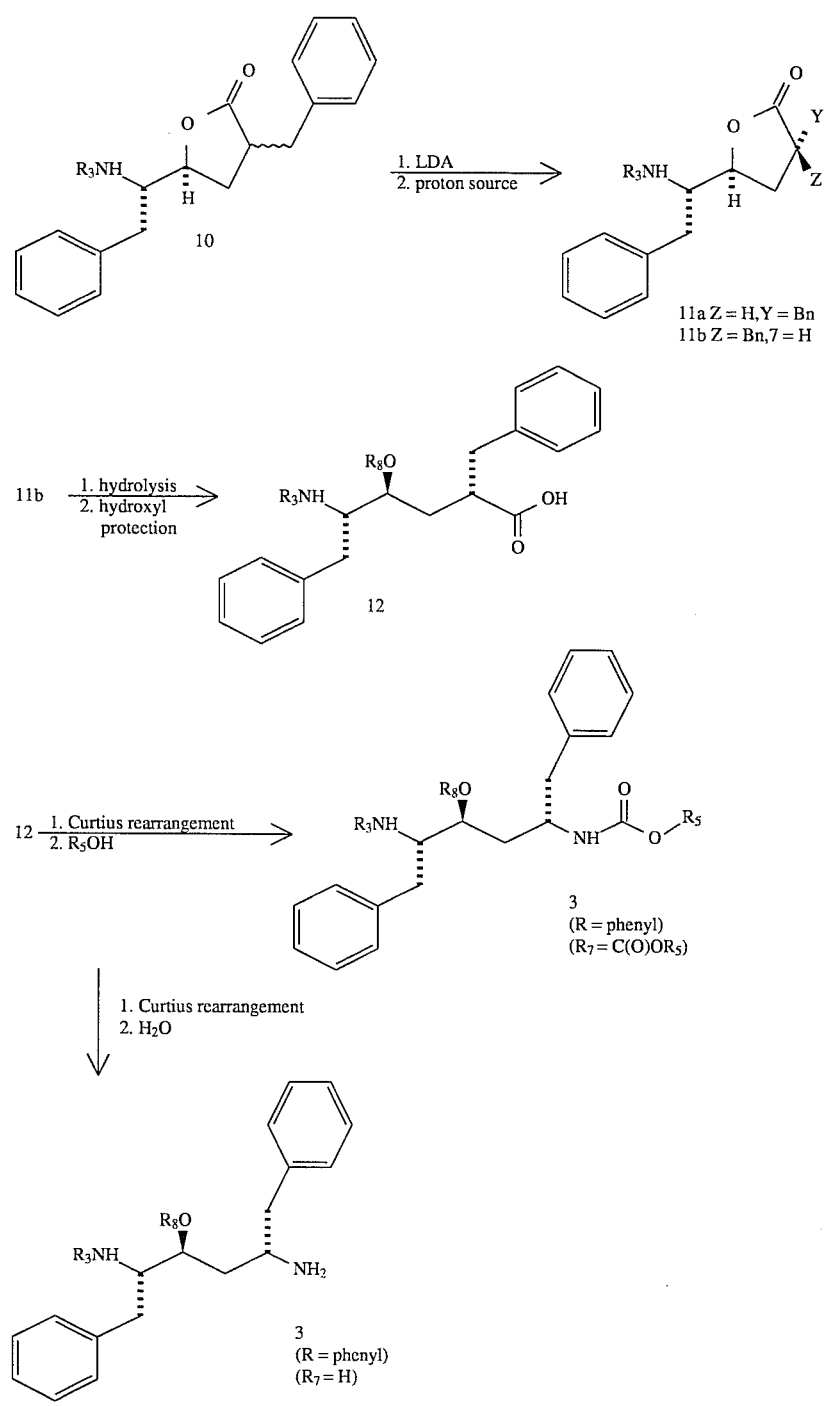

SCHEME IV

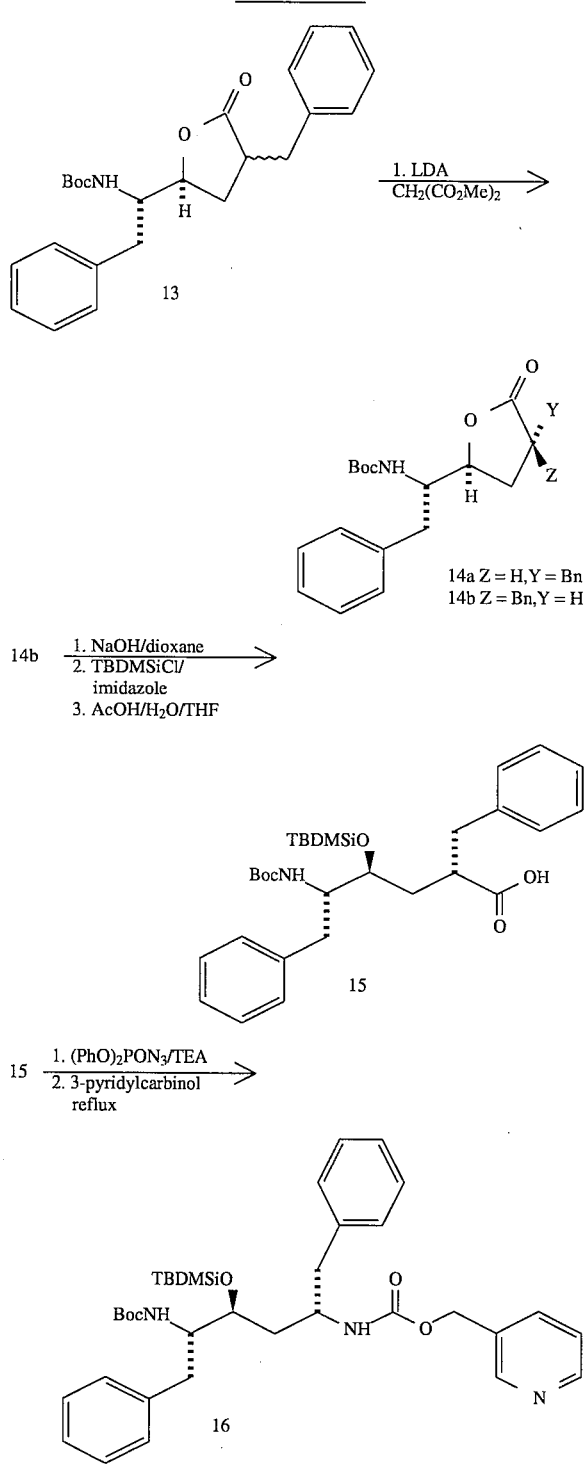

14a Z = H, Y = Bn
14b Z = Bn, Y = H

The term "loweralkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "cycloalkyl" as used herein refers to an aliphatic ring having 3 to 7 carbon atoms including, but not limited to, cyclopropyl, cyclobutyl, cyclopentyl, cyclohexyl and the like. Cycloalkyl groups can be unsubstituted or substituted with one or two substituents independently selected from loweralkyl, halo, amine, N-protected amine, alkylamino, N-protected alkylamino, hydroxy, —$OR_{30}$ wherein $R_{30}$ is a hydroxy-protecting group, alkoxy, thioalkoxy, alkoxyalkyl, thioalkexyalkyl and —OR wherein R is (heterocyclic)alkyl.

The term "(pyridyl)methyl" as used herein refers to 2-pyridylmethyl, 3-pyridylmethyl or 4-pyridylmethyl.

The term "(thiazolyl)methyl" as used herein refers to 2-thiazelylmethyl, 4-thiazolylmethyl or 5-thiazolylmethyl.

The term "aryl" as used herein refers to phenyl, naphthyl, tetrahydronaphthyl, indanyl or indenyl. Aryl groups can be unsubstituted or substituted with one or two substituents independently selected from loweralkyl, halo, amine, N-protected amine, alkylamino, N-protected alkylamino, hydroxy, —$OR_{30}$ wherein $R_{30}$ is a hydroxy-protecting group, alkoxy, thioalkoxy, alkoxyalkyl, thioalkoxyalkyl and —OR wherein R is (heterocyclic)alkyl.

The term "alkoxy" as used herein refers to —$OR_{20}$ wherein $R_{20}$ is a loweralkyl group.

The term "alkoxyalkyl" as used herein refers to a loweralkyl radical to which is appended an alkoxy group.

The term "thioalkoxy" as used herein refers to -$SR_{21}$ wherein $R_{21}$ is a loweralkyl group.

The term "thioalkoxyalkyl" as used herein refers to a loweralkyl radical to which is appended a thioalkoxy group.

The term "halo" as used herein refers to F, Cl, Br or I.

The term "alkylamino" as used herein refers to —$NHR_{22}$ wherein $R_{22}$ is a loweralkyl group.

The term "heterocyclic" as used herein refers to a 5-membered or 6-membered aromatic or saturated ring containing one or two heteroatoms independently selected from N, O and S, the remaining ring atoms being carbon atoms. Heterocyclics can be unsubstituted or substituted with one or two substituents independently selected from loweralkyl, halo, amino, N-protected amino, alkylamino, N-protected alkylamino, hydroxy, —$OR_{31}$ wherein $R_{31}$ is a hydroxy-protecting group, alkoxy, thioalkoxy, alkoxyalkyl and thioalkoxyalkyl. In addition, saturated heterocyclics can be substituted with oxo (==O). In addition, nitrogen-containing saturated heterocyclic rings can be N-protected and sulfur-containing saturated heterocyclic rings can be S-oxidized. Heterocyclics include, pyridyl, pyrimidinyl, pyrazinyl, thiazolyl, imidazolyl, oxazolyl, isoxazolyl, isothiazolyl, dioxanyl, dioxolanyl, furyl, thienyl, pyrrolyl, tetrahydropyranyl, tetrahydrofuranyl, tetrahydrothiophene, tetrahydrothiopyran, morpholinyl, thiomorpholinyl, piperazinyl, piperidinyl and pyrrolidinyl.

The term "N-protecting group" or "N-protected" as used herein refers to those groups intended to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise carbamates, amides, N-alkyl derivatives, amino acetal derivatives, N-benzyl derivatives, imine derivatives, enamine derivatives and N-heteroatom derivatives. N-protecting groups include formyl, acetyl, benzoyl, pivaloyl, t-butylacetyl, phenylsulfonyl, benzyl, t-butyloxycarbonyl (Boc), benzyloxycarbonyl (Cbz) and the like.

The term "hydroxy-protecting group" as used herein refers to a substituent which protects hydroxyl groups against undesirable reactions during synthetic procedures such as those hydroxy-protecting groups disclosed in Greene, "Protective Groups In Organic Synthesis," (John Wiley & Sons, New York (1981)). Hydroxy-protecting groups comprise substituted methyl ethers, for example, methoxymethyl, benzyloxymethyl, 2-methoxyethoxymethyl, 2-(trimethylsilyl)ethoxymethyl, t-butyl, benzyl and triphenylmethyl; tetrahydropyranyl ethers; substituted ethyl ethers, for example, 2,2,2-trichloroethyl; silyl ethers, for example, trimethylsilyl, t-butyldimethylsilyl and t-butyldiphenylsilyl; and esters prepared by reacting the hydroxyl group with a carboxylic acid, for example, acetate, propionate, benzoate and the like.

The compounds of the formula 3 can be used in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate.

Examples of acids which may be employed to form acid addition salts include such inorganic acids as hydrochloric acid, sulphuric acid and phosphoric acid and such organic acids as oxalic acid, maleic acid, succinic acid and citric acid.

The following examples will serve to further illustrate the process of the invention.

EXAMPLE 1

(2R,4S,5S) and
(2S,4S,5S)-2-Benzyl-5-[(tert-butyloxycarbonyl)
amino]-6 -phenyl-4-hydroxyhexanolide (1a and 1b)

A diastereomeric mixture of (2RS,4S,5S)-2-Benzyl-5-[(tertbutyloxycarbonyl)amino]-6-phenyl-4-hydroxyhexanolide (J. Org. Chem. 51 3921 (1986)) (1.0 g, 2.5 mmol) in 7.5 ml of THF was added dropwise to LDA (5.5 mmol, prepared by dropwise addition of 2.5M n-BuLi (5.5 mmol) to a solution of diisopropyl amine (5.5 mmol) in 7.5 ml of THF at −60° C. and then stirred for 10 min. at −78° C.) at −78° C. The reaction mixture was stirred for 20 min. and diethyl malonate (1.4 ml, 12.5 mmol) was added. The reaction mixture was then stirred for 20 min. at −78° C., warmed to room temperature and quenched with saturated ammonium chloride. The aqueous phase was extracted with diethyl ether. The extracts were combined, washed with saturated sodium chloride, dried over magnesium sulfate and concentrated to afford an oil which was purified by chromatography (3:1 hexane/EtOAc). Lactones 1b (2S) and 1a (2R) were isolated in a ratio of 9.5:1 and were identical by TLC and $^1$H NMR to authentic lactones previously prepared (J. Org. Chem. 51 3921 (1986). 1a: 67 mg (7%); $R_f$=0.32 4:1 hexanes/EtOAc. 1b: 634 mg (64 %); $R_f$=0.23 4:1, hexane/EtOAc.

EXAMPLE 2

(2S,4S,5S)
2-Benzyl-5-[(tert-butyloxycarbonyl)amino]-
6-phenyl-4-hydroxyhexanoic Acid
tert-Butyldimethylsilyl Ether A solution of 1b (630 mg, 1.59 mmol) and NaOH 1.0M (1.75 mL, 1.75 mmol) in of 8 mL of dioxane and 4 mL of water was stirred vigorously for 30 min. The solution was concentrated and the residue was treated with 10% aqueous citric acid to bring the pH to 2. The aqueous phase was extracted with diethyl ether (3×20 mL). The extracts were combined, washed with saturated NaCl, dried ($Na_2SO_4$), and concentrated to give the crude carboxylic acid.

The crude acid was immediately combined with TBDMSiCl (1.2 g, 8 mmol) and imidazole (950 mg, 14 mmol) in 5 mL of DMF and stirred overnight at ambient temperature. The solution was concentrated and the residue partitioned between water and diethyl ether. The pH of the solution was adjusted to 4 with 10% aqueous citric acid and the aqueous phase was extracted with diethyl ether (3×20 mL). The organic extracts were combined, washed with saturated NaCl, dried ($Na_2SO_4$), and concentrated to give 710 mg (70%) of the crude diTBDMSi ether/ester.

The crude diTBDMSi ether/ester (710 mg, 1.1 mmol) was stirred in a mixture of 9 mL of glacial acetic acid, 3 ml of THF and 3 mL of water for 2 h at ambient temperature and concentrated. The residue was treated with ice water and extracted with diethyl ether (3×20 mL). The extracts were combined, washed with saturated NaCl, dried ($Na_2SO_4$), and concentrated. The crude product was purified by chromatography (6:94 MeOH/$CH_2CH_2$) to give 240 mg (41%) of acid. mp 118°–119° C.; $^1$H NMR ($CDCl_3$) δ0.09 (s, 6H), 0.93 (s, 9H), 1.35 (s, 9H), 1.65–1.92 (m, 3H), 2.64–2.98 (m, 5H), 3.71 (m, 1H), 4.04 (m, 1H), 4.63 (m, 1H), 7.08–7.28 (arom, 10H); LRMS, m/e 528 ($M^+$), 545 ($M+NH_4^+$). Anal. Calcd for $C_{30}H_{45}NO_5Si$: C, 68.27; H, 8.59; N, 2.65 Found: C, 68.56; H, 8.73; N, 2.63.

EXAMPLE 3

(2S,3S,5S)
2-[(tert-Butyloxycarbonyl)amino]-1,6-diphenyl-
3-hydroxy-5-[(3
-pyridinylmethoxycarbonyl)amino]hexane
tert-Butyldimethylsilyl Ether A solution of the product of Example 2 (105 mg, 0.20 mmol), triethylamine (22 mg, 31 μL, 0.22 mmol) and diphenylphosphoryl azide (147 μL, 0.22 mmol) in 2 mL of dry toluene was heated at 70° C. for 1.5 h. To the solution was added 3-pyridylcarbinol (440 μL, 4.52 mmol) and the solution was heated at reflux temperature for 36 h, cooled and concentrated. The residue was partitioned between EtOAc and water. The organic layer was washed with 10 mL of 1M HCl, 10 mL water, 10 mL of $NaHCO_3$, saturated NaCl, dried ($MgSO_4$), and concentrated. The crude product was purified by chromatography (1.5:1, hexanes/EtOAc) to give 81 mg (64%) of the desired carbamate. $R_f$=0.31, 3:2 hexane/ethyl acetate; $^1$H NMR ($d_6$ DMSO) δ0.05 (s, 6H), 0.90 (s, 9H), 1.30 (s, 9H), 1.49–1.75 (m, 3H), 2.58–2.73 (bm, 4H), 3.68–4.00 (bm, 3H), 4.80–5.08 (m, 2H), 6.44 (bd, J=9 Hz, 1H), 7.10–7.38 (m, 11H), 7.62 (bm, 1H), 8.50 (m, 2H); $^{13}$C NMR (75 MHz $d_6$ DMSO) δ17.72, 25.82, 27.71, 28.19, 35.58, 49.28, 54.29, 62.47, 71.48, 77.46, 123.28, 125.62, 125.80, 127.82, 127.89, 128.79, 128.91, 132.92, 135.29, 138.93, 139.63, 148.84, 148.89, 155.26, 155.38; LRMS m/e 634 ($M+H^+$); HRMS Calcd for $C_{36}H_{52}N_3O_5Si$: 634.3676. Found 634.3687. Anal. Calcd for $C_{36}H_{51}N_3O_5Si$*0.25 $H_2O$: C, 67.73; H, 8.13; N, 6.58. Found: C, 67.58; H, 7.98; N, 6.46.

EXAMPLE 4

4A. (5S,1'S)-5-(1-(Boc-amino)-2-
phenylethyl)dihydrofuran- 2(3H)-one

A mixture of 10.6 g (46.6 mmol) of ethyl 3-iodopropionate, 4.9 g (75.3 mmol) of freshly prepared zinc-copper couple, 7.9 ml of dimethylacetamide and 79 ml of dry toluene was stirred under $N_2$ atmosphere at ambient temperature for 1 h and at 80° C. for 4 h. The mixture was cooled to 20° C. and the excess zinccopper couple allowed to settle. To a dry flask was added 10 ml of dry toluene, 56 ml of dry dichloromethane and 3.4 ml (11.4 mmol) of titanium isopropoxide. The solution was cooled to 15° C. and 3.6 ml (32.8 mmol) of titanium chloride was added dropwise (<25° C.). The solution was stirred at ambient temperature for 15 min, and then cooled to −40° C. The iodozinc-homoenolate supernatant was added by cannula to it (<25° C.). The resulting dark-red solution was stirred at −25° C. for 5 min and then cooled to −40° C. A solution of 5.5 g (22.1 mmol) of Boc-L-phenylalaninal in 20 ml of dichloromethane was added by cannula to it (<−40° C.). The reaction mixture was stirred vigorously at −20° C. for 24 h. The reaction was quenched by addition to a stirred mixture of 250 ml of water and 350 ml of tert-butyl methyl ether at 0° C. The aqueous phase was extracted with 250 ml of tert-butyl methyl ether. The combined organic phases were washed with water, saturated aqueous $NaHCO_3$, water and brine, dried over $MgSO_4$ and concentrated in vacuo to give crude hydroxyester as a white solid. The hydroxyester was dissolved in 180 ml of toluene and 5.5 ml of acetic acid and heated at reflux for 2.5 h. The mixture was cooled to ambient temperature, diluted with isopropyl acetate, washed with water, saturated aqueous $NaHCO_3$, water and brine, dried over $MgSO_4$ and concentrated in vacuo to give an oil which was crystallized from hexane to provide 5.95 g (88%) of desired compound as a white solid. $^1H$ NMR ($CDCl_3$) δ1.37 (s, 9H), 2.14 (m, 2H), 2.52 (m, 2H), 2.84–3.00 (m, 2H), 4.01 (m, 1H), 4.47 (td, 1H), 4.59 (br d, 1H), 7.24–7.32 (m, 5H). Mass spectrum: $(M+H)^+=323$.

4B. (5S,1'S)-3-carboethoxy-5-(1-(Boc-amino)-2-phenylethyl)dihydrofuran-2(3H)-one LDA was prepared by dropwise addition of 7.4 ml (18.6 mmol) of 2.5M n-BuLi to a solution of 2.60 ml (18.6 mmol) of diisopropyl amine in 25 ml of dry tetrahydrofuran at −78° C. The LDA solution was stirred for 20 min at −78° C. and 2.70 g (8.84 mmol) of the resultant compound of Example 4A in 25 ml of dry tetrahydrofuran was added dropwise. The reaction mixture was stirred for 20 min at −78° C. and 210 ml (22.1 mmol) of ethyl chloroformate was then added. After being stirred at −78° C. for 5 h, the reaction was quenched with saturated aqueous $NH_4Cl$, extracted with three 50 ml portions of dichloromethane. The combined organic layers were dried over $Na_2SO_4$, concentrated in vacuo and the residue was purified by silica gel chromatography using 25% ethyl acetate in hexane to provide 2.10 g (63%) of the desired compound as a white solid. Mass spectrum: $(M+H)^+=378$.

4C. (5S,1'S)-3-carboethoxy-3-((4-pyridinyl)methyl-5-(1-(Boc-amino)-2-phenylethyl)dihydrofuran-2(3H)-one A solution of 110.0 mg (4.78 mmol) of sodium in 5 ml of absolute ethanol was added to a solution of 0.81 g (2.15 mmol) of the resultant compound of Example 4B in 10 ml of absolute ethanol. The mixture was stirred at ambient temperature for 20 min and 4-picolyl chloride hydrochloride was then added to it. After being stirred at 50°–60° C. for 24 h, the reaction was cooled in an ice bath, neutralized with 10% citric acid to pH ~6 and extracted with four 30 ml portions of dichloromethane. The combined organic layers were added over $Na_2SO_4$, concentrated in vacuo and the residue was purified by silica gel chromatography using 10% methanol in dichloromethane to provide 838.6 mg (83%) of the desired compound as a white foamy solid. Mass spectrum: $(M+H)^+=469$.

4D. (5S,1'S)-3-((4-pyridinyl)methyl)-5-(1-(Boc-amino)-2-phenylethyl)dihydrofuran-2(3H)-one A solution of 838.0 mg (1.79 mmol) of the resultant compound of Example 4C in 10 ml of dimethoxyethane was treated with 7.2 ml (7.20 mmol) of 1M aqueous lithium hydroxide. After being stirred at ambient temperature for 24 h, the bulk of the 1,2-dimethoxyethane was removed in vacuo. The remaining mixture was neutralized to pH ~6 with 10% citric acid and extracted with four 20 ml portions of dichloromethane. The combined organic layers were dried over $Na_2SO_4$ and concentrated in vacuo to give the crude acid. The acid was dissolved in 10 ml of toluene, heated at reflux for 15 h. The solvent was removed in vacuo, and the residue was purified by silica gel chromatography using 10% methanol in dichloromethane to provide 398.1 mg (56%) of the desired compound (3S and 3R mixture) as a white foamy solid. Mass spectrum: $(M+H)^+=397$.

4E. (4S,5S)-5-(Boc-amino)-6-phenyl-2-((4-pyridinyl)methyl)-4-(tert-butyldimethylsilyloxy)hexanoic acid A solution of 396.0 mg (1.0 mmol) of the resultant compound of Example C1D in 24 ml of a 2:1 mixture of 1,2-dimethoxyethane and water was treated with 4 ml of 1M aqueous lithium hydroxide. After being stirred at ambient temperature for 1.5 h, the bulk of the 1,2-dimethoxyethane was removed in vacuo. The remaining mixture was neutralized to pH ~6 with 10% citric acid and extracted with four 20 ml portions of dichloromethane. The combined organic layers were dried over $Na_2SO_4$ and concentrated in vacuo to give 382.3 mg of the crude hydroxy acid. This hydroxy acid was dissolved in 4 ml of dry DMF and 706.0 mg (4.68 mmol) of tert-butyldimethylsilyl chloride and 600.0 mg (8.81 mmol) of imidazole were added. After being stirred at ambient temperature for 18 h, 8 ml of MeOH was added to the mixture. Stirring was continued for 4 h and the solvents were then removed in vacuo. The residue was treated with 5 ml of water, neutralized to pH ~6 with 10% citric acid and extracted with four 20 ml portions of dichloromethane. The combined organic layers were dried over $Na_2SO_4$, concentrated in vacuo and the residue was purified by silica gel chromatography using 10% methanol in dichloromethane to provide 336.9 mg (64%) of the desired compound (2S and 2R mixture) as a white foamy solid. Mass spectrum: $(M+H)^+=529$.

4F. (2S,3S,5S)-2-(Boc-amino)-5-(N-((3-pyridirlyl)methoxy-carbonyl)amino)-1-phenyl-6-(4-pyridinyl)-3-(tert-butyl-dimethylsilyloxy)hexane and (2S,3S,5R)-2-(Boc-amino)-

5-(N-((3-pyridinyl)methoxycarbonyl)amino)-1-phenyl-6-(4-pyridinyl)-3-(tertbutyldimethylsilyloxy)hexane A solution of 324.0 mg (0.613 mmol) of the resultant compound of Example 4E, 264 µl (1.22 mmol) of diphenylphosphoryl azide, 149 µl (1.53 mmol) of 3-pyridylcarbinol and 213 µl (1.53 mmol) of triethylamine and in 3 ml of dioxane was heated at 75°–80° C. for 20 h. The solvents were then removed in vacuo and the residue was purified by silica gel chromatography using 10% methanol in dichloromethane to provide 121.2 mg (31%) of (2S,3S,5S)-2-(Boc-amino)-5-(N-((3-pyridinyl)methoxycarbonyl)amino)-1-phenyl-6-(4-pyridinyl)-3-(tert-butyldimethylsilyloxy)hexane and 50.9 mg (13%) of (2S, 3S,5R)-2-(Boc-amino)-5-(N-((3-pyridinyl)methoxycarbonyl)amino)-1-phenyl-6-(4-pyridinyl)-3-(tert-butyldimethylsilyloxy)hexane as a white solid. Mass spectrum: $(M+H)^+=635$.

4G. (2S,3S,5S)-2-(Boc-amino)-5-(N-((3-pyridinyl)methoxy-carbonyl)amino)-1-phenyl-6-(4-pyridinyl)-3-hydroxyhexane A solution of 74.5 mg (0.117 mmol) of (2S,3S,5S)-2-(Boc-amino)-5-(N-((3-pyridinyl)methoxycarbonyl)amino)-1-phenyl-6-(4-pyridinyl)-3 -(tert-butyldimethylsilyloxy)-hexane in 4 ml of tetrahydrofuran was treated with 102 µl of 1M solution of tetrabutylammonium fluoride in tetrahydrofuran. After being stirred at ambient temperature for 24 h, the solvent was removed in vacuo, and the residue was purified by silica gel chromatography using 10% methanol in dichloromethane to provide 51.4 mg (84%) of the desired compound as a white solid. $^1$H NMR (CDCl$_3$) δ1.37 (s, 9H), 1.65 (t, 2H), 2.82–3.01 (m, 5H), 3.70 (m, 2H), 4.03 (m, 1H), 4.78 (d, 1H), 5.03 (s, 2H), 5.18 (br d, 1H), 7.06 (d, 2H, 7.16–7.31 (m, 6H), 7.61 (d, 1H), 8.44 (d, 2H), 8.57 (s , 2H). Mass spectrum: $(M+H)^+=521$.

4H. (2S,3S,5S)-2-amino-5-(N-((3-pyridinyl)methoxycarbonyl)-amino)-1-phenyl-6-(4-pyridinyl)-3-hydroxyhexane A solution of 50.2 mg (0.096 mmol) of the resultant compound of Example 4G in 1.5 ml of dichloromethane was treated with 0.5 ml of trifluoroacetic acid. After being stirred at ambient temperature for 2 h, the solvents were removed in vacuo. The residue was dissolved in 20 ml of dichloromethane, washed with saturated aqueous NaHCO$_3$, dried over Na$_2$SO$_4$, and concentrated in vacuo to give 39.2 mg (97%) of the crude desired compound as a off white solid.

EXAMPLE 9

5A. (5S,1'S)-3-((3-furyl)methyl)-5-(1-(Boc-amino)-2-phenylethyl)-dihydrofuran-2(3H)-one LDA was prepared by dropwise addition of 4.1 ml (18.6 mmol) of 2.5M n-BuLi to a solution of 2.60 ml (10.3 mmol) of diisopropyl amine in 10 ml of dry tetrahydrofuran at –78° C. The LDA solution was stirred for 30 min at –78° C. and 1.50 g (4.91 mmol) of the resultant compound of Example 4A in 10 ml of dry tetrahydrofuran was added dropwise. The reaction mixture was stirred for 30 min at –78° C. and 0.76 ml (7.37 mmol) of 3-bromomethylfuran was then added. After being stirred at –78° C. for 5 h, the reaction was quenched with saturated aqueous NH$_4$Cl, extracted with four 20 ml portions of dichloromethane. The combined organic layers were dried over Na$_2$SO$_4$, concentrated in vacuo and the residue was purified by silica gel chromatography using 25% ethyl acetate in hexane to provide 1.49 g (79%) of the desired compound (3S and 3R mixture) as a pale yellow oil. Mass spectrum: $(M+NH_4)^+=403$.

5B. (3S,5S,1'S)-3-((3-furyl)methyl)-5-(1-(Boc-amino)-2-phenylethyl)-dihydrofuran-2(3H)-one LDA was prepared by dropwise addition of 1.59 ml (3.97 mmol) of 2.5M n-BuLi to a solution of 0.58 ml (4.16 mmol) of diisopropyl amine in 7 ml of dry tetrahydrofuran at –78° C. The LDA solution was stirred for 30 min at –78° C. and 728.7 mg (1.89 mmol) of the resultant compound of Example 5A in 7 ml of dry tetrahydrofuran was added dropwise. The reaction mixture was stirred for 30 min at –78° C. and 1.41 ml (5.67 mmol) of dibenzylmalonate was then added. After being stirred at –78° C. for 30 min, the reaction was warmed to ambient temperature and then quenched with saturated aqueous NH$_4$Cl, extracted with three 20 ml portions of dichloromethane. The combined organic layers were dried over Na$_2$SO$_4$, concentrated in vacuo and the residue was purified by silica gel chromatography using 25% ethyl acetate in hexane to provide 540.8 mg (74%) of the desired compound as a colorless oil. $^1$H NMR (CDCl$_3$) δ1.50 (s, 9H), 1.83 (m, 1H), 2.14 (m, 1H), 2.69 (m, 1H), 2.77–2.99 (m, 4H), 3.95 (m, 1H), 4.34 (m, 1H), 4.52 (br d, 1H), 6.25 (s, 1H), 7.21–7.34 (m, 7H).

5C. (2S,4S,5S)-5-(Boc-amino)-6-phenyl-2-((3-furyl)methyl)-4-(tert-butyldimethylsilyloxy)hexanoic acid Using the procedure of Example 4E but replacing the resultant compound of Example 4D with the resultant compound of Example 5B provided, after silica gel chromatography using 5% methanol in dichloromethane, 830.1 mg (74%) of the desired compound as a yellow oil.

5D. (2S,3S,5S)-2-(Boc-amino)-5-(N-((3-pyridinyl)methoxy- carbonyl)amino)-1-phenyl-6-(3-furyl)-3-(tert-butyl-dimethylsilyloxy)hexane Using the procedure of Example 4F but replacing the resultant compound of Example 4E with the resultant compound of Example 4C provided, after silica gel chromatography using 5% methanol in dichloromethane, 689.0 mg (83%) of the desired compound as a yellow oil.

5E. (2S,3S,5S)-2-(Boc-amino)-5-(N-((3-pyridinyl)methoxy,carbonyl)amino)-1-phenyl-6-(3-furyl)-3-hydroxyhexane Using the procedure of Example 4G but replacing (2S, 3S,5S)-2-(Boc-amino)-5-(N-((3-pyridinyl)methoxy-carbonyl)amino)-1-phenyl-6-(4-pyridinyl)-3 -(tert-butyl-dimethylsilyloxy)hexane with the resultant compound of Example 5D provided, after silica gel chromatography using 5% methanol in dichloromethane, 334.5 mg (60%) of the desired compound as a white solid.
$^1$H NMR (CDCl$_3$) δ1.38 (s, 9H), 1.66 (t, 2H), 2.61 (d, 2H), 2.85 (t, 3H), 3.70 (m, 2H), 3.89 (m, 1H), 4.84 (br d, 1H), 5.07 (br, 1H), 5.12 (s, 2H), 7.14–7.31 (m, 7H), 7.40 (m, 1H), 7.76 (br d, 1H), 8.57 (dd, 1H), 8.64 (br s, 1H). Mass spectrum: $(M+H)^+=510$.

5F. (2S,3S,5S)-2-amino-5-(N-((3-pyridinyl)methoxycarbonyl)-amino)-1-phenyl-6-(3-furyl)-3-hydroxyhexane Using the procedure of Example 4H but replacing the resultant compound of Example 41G with the resultant compound of Example 5E provided 113.2 mg (94%) of the desired compound as a off white solid.

EXAMPLE 6

6A. (5S,1'S)-3-carboethoxy-3-((5-thiazolyl)methyl-5-(1-(Boc-amino)-2-phenylethyl)dihydrofuran-2(3H)-one Using the procedure of Example 4C but replacing 4-picolyl chloride hydrochloride with 5-chloromethylthiazole hydrochloride provided 881.7 mg (47%) of the desired compound as a white solid. Mass spectrum: $(M+H)^+=475$.

6B. (5S,1'S)-3-((5-thiazolyl)methyl-5-(1-(Boc-amino)-2-phenylethyl)dihydrofuran-2(3H)-one Using the procedure of Example 4D but replacing the resultant compound of Example 4C with the resultant compound of Example 6A provided, after silica gel chromatography using 5% methanol in dichloromethane, 222.6 mg (32%) of the desired compound (3S and 3R mixture) as a white solid. Mass spectrum: $(M+H)^+=403$.

6C. (3S,5S,1'S)-3-((5-thiazolyl)methyl)-5-(1-(Boc-amino)-2-phenylethyl)-dihydrofuran-2(3H)-one Using the procedure of Example 5B but replacing the resultant compound of Example 5A with the resultant compound of Example 6B provided, after silica gel chromatography using 50% ethyl acetate in hexane, 117.2 mg (55%) of the desired compound as a yellow oil. $^1$H NMR (CDCl$_3$) δ1.40 (s, 9H), 1.84 (m, 1H), 2.21 (ddd, 1H), 2.82–2.99 (m, 3H), 3.07 (dd, 1H), 3.43 (dd, 1H), 3.97 (br q, 1H), 4.36 (ddd, 1H), 4.55 (br d, 1H), 7.21–7.33 (m, 5H), 7.63 (s, 1H), 8.69 (s, 1H).

6D. (2S,4S,5S)-5-(Boc-amino)-6-phenyl-2-((5-thiazolyl)-methyl)-4-(tert-butyldimethylsilyloxy)hexanoic acid Using the procedure of Example 4E but replacing the resultant compound of Example 4D with the resultant compound of Example 6C provided, after silica gel chromatography using 10% methanol in dichloromethane, 111.6 mg (75%) of the desired compound as a white solid.

6E. (2S,3S,5S)-2-(Boc-amino)-5-(N-((3-pyridinyl)methoxy-carbonyl)amino)-1-phenyl-6-(5-thiazolyl)-3-(tert-butyl-dimethylsilyloxy)hexane Using the procedure of Example 4F but replacing the resultant compound of Example 4E with the resultant compound of Example 6D provided, after silica gel chromatography using 10% methanol in dichloromethane, 116.1 mg (92%) of the desired compound as a yellow oil. Mass spectrum: $(M+H)^+=641$.

6F. (2S,3S,5S)-2-(Boc-amino)-5-(N-((3-pyridinyl)methoxy-carbonyl)amino)-1-phenyl-6-(5-thiazolyl)-3-hydroxyhexane Using the procedure of Example 4G but replacing (2S,3S,5S)-2-(Boc-amino)-5-(N-((3-pyridinyl)methoxy-carbonyl)amino)-1-phenyl-6-(4-pyridinyl)-3-(tert-butyl-dimethylsilyloxy)hexane with the resultant compound of Example 6E provided, after silica gel chromatography using 5% methanol in dichloromethane, 64.2 mg (72%) of the desired compound as a white solid. $^1$H NMR (CDCl$_3$) δ1.38 (s, 9H), 1.64 (m, 2H), 2.87 (m, 2H), 3.08 (m, 2H), 3.68 (m, 2H), 3.96 (m, 1H), 4.75 (br d, 1H), 5.10 (dd, 2H), 5.15 (br, 1H), 7.17–7.33 (m, 7H), 7.53 (s, 1H), 7.66 (br d, 1H), 8.58 (m, 2H), 8.66 (s, 1H).

6G. (2S,3S,5S)-2-amino-5-(N-((3-pyridinyl)methoxycarbonyl)-amino)-1-phenyl-6-(5-thiazolyl)-3-hydroxyhexane Using the procedure of Example 4H but replacing the resultant compound of Example 4G with the resultant compound of Example 6F provided 48.0 mg (99%) of the desired compound as a off white solid.

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. A process for the preparation of the 2S,3S,5S compound of the formula:

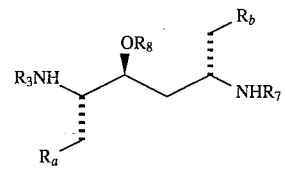

wherein $R_a$ and $R_b$ are independently selected from loweralkyl, cycloalkyl, alkoxylalkyl, thioalkoxyalkyl, aryl and heterocyclic, $R_3$ is hydrogen or an N-protecting group, $R_7$ is hydrogen or —C(O)—O—$R_5$ wherein $R_5$ is selected from benzyl, (thiazolyl)methyl and (pyridyl)methyl and $R_8$ is hydrogen or a hydroxy-protecting group; or a salt thereof, comprising (a) reaction of the compound of the formula:

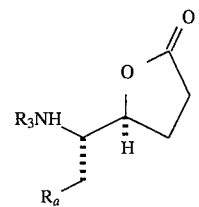

with XCH$_2$R$_b$, wherein X is a leaving group to produce a diastereomeric mixture of the compound of the formula:

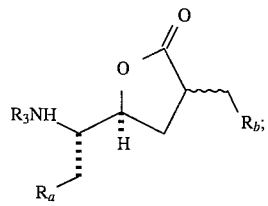

(b) reaction of the product of step (a) with strong base, followed by reaction with a hydroxy-protecting reagent, to provide a diastereomeric mixture of the compound of the formula:

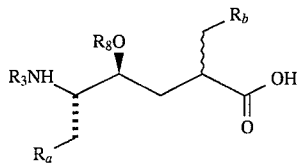

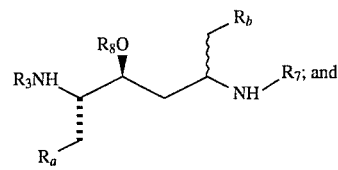

wherein $R_8$ is a hydroxy-protecting group;

(c) reaction of the product of step (c) with diphenylphosphoryl azide, followed by reaction with $R_5OH$ wherein $R_7$ is $-C(O)-O-R_5$ or reaction with $H_2O$ wherein $R_7$ is hydrogen to provide a diastereomeric mixture of the compound of the formula:

(d) separation of the desired 2S,3S,5S compound.

2. The process of claim 1 wherein $R_3$ is t-butyloxycarbonyl and $R_8$ is t-butyldimethylsilyl.

* * * * *